(12) United States Patent
Lee et al.

(10) Patent No.: US 12,218,489 B2
(45) Date of Patent: Feb. 4, 2025

(54) EXPOSED ELECTRODE NEGATIVE AIR ION DEVICE WITH FIBROUS MAT SURFACE MOUNTABLE IN AN EXPOSED ENVIRONMENT

(71) Applicant: TEMASEK LIFE SCIENCES LABORATORY LIMITED, Singapore (SG)

(72) Inventors: Kheng Nam Lee, Singapore (SG); Sharvin Kumar S/O N Arjunan, Singapore (SG); Swain Stephen, Singapore (SG); Hean Chuan Fong, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 18/036,647

(22) PCT Filed: Oct. 12, 2021

(86) PCT No.: PCT/SG2021/050615
§ 371 (c)(1),
(2) Date: May 12, 2023

(87) PCT Pub. No.: WO2022/103327
PCT Pub. Date: May 19, 2022

(65) Prior Publication Data
US 2023/0420920 A1 Dec. 28, 2023

(30) Foreign Application Priority Data
Nov. 13, 2020 (SG) .......................... 10202011322W

(51) Int. Cl.
*H01T 23/00* (2006.01)
*H01T 19/00* (2006.01)

(52) U.S. Cl.
CPC .............. *H01T 23/00* (2013.01); *H01T 19/00* (2013.01)

(58) Field of Classification Search
None
See application file for complete search history.

(56) References Cited

U.S. PATENT DOCUMENTS

2005/0269519 A1   12/2005   Kim et al.
2012/0305799 A1   12/2012   Sung et al.
(Continued)

FOREIGN PATENT DOCUMENTS

CN   111493582 A   8/2020
JP   2004351299 A   12/2004

OTHER PUBLICATIONS

International Search Report and Written Opinion of International Searching Authority completed on Jan. 11, 2022 for International Application No. PCT/SG2021/050615.
(Continued)

*Primary Examiner* — Stephen W Jackson
(74) *Attorney, Agent, or Firm* — JCIP; Joseph G. Chu

(57) ABSTRACT

An exposed electrode negative air ion device, either stand-alone or mounted in an exposed environment 56 as part of a negative air ion panel system 50. Each device comprises: (a) an electronics module 22, the electronics module 22 including a negative voltage generator 22B; and (b) an exposed electrode 10, the exposed electrode 10 including a mat surface 11 of intertwined individual fibres electrically connected to the negative voltage generator 22B. The mat surface 11 has a minimum mean resistance of $R_{MIN}$ to restrict a maximum capacitive current discharge below a capacitive current discharge detection threshold. The negative voltage generator 22B is configured to generate a negative voltage source 23 from a power supply 21 within a set of electrical parameters. The set of electrical param-
(Continued)

eters includes a maximum preset negative voltage of $V_{MAX}$ and a maximum operating current, the maximum operating current set below or equal to a direct current detection threshold.

24 Claims, 9 Drawing Sheets

(56) References Cited

U.S. PATENT DOCUMENTS

| | | | |
|---|---|---|---|
| 2016/0051713 A1* | 2/2016 | Robert | C02F 1/4608 |
| | | | 361/231 |
| 2016/0221002 A1* | 8/2016 | Lin | B03C 3/363 |
| 2022/0352696 A1* | 11/2022 | Walsh | H01T 23/00 |

OTHER PUBLICATIONS

Kono Michinari Mchkono@Acm Org et al: 1-15 ADD. "Design Guideline for Developing Safe Systems that Apply Electricity to the Human Body", ACM Transactions On Computer—Human Interaction, ACM, New York, NY, US, vol. 25, No. 3, Jun. 8, 2018 (Jun. 8, 2018), pp. 1-36, XP058681370, ISSN: 1073-0516, DOI: 10.1145/3184743 * p. 1-p. 36 *.

Extended European Search Report dated Sep. 11, 2024 for European Application No. 21892443.9.

* cited by examiner

MAXIMUM SURFACE AREA OF
SINGLE CHARGED DISK PLATE 3-00 ⇩

$Q_{TH} = C_{PANEL} \times V_{MAX}$      *Equation 2* where:

$Q_{TH}$ = charge discharge detection threshold $C_{PANEL}$ = self-capacitance of exposed electrode panel $V_{MAX}$ = maximum preset negative voltage $C_{PANEL} = 8\epsilon_0 r_D$      *Equation 3a* where:

$r_D$ = radius of single charged disk $\epsilon_0$ = permittivity of free space, approximately $8.85 \times 10^{-12}$ F·m$^{-1}$ $A_{MAX} = \pi \times r_D^2$      *Equation 3b* where:

$A_{MAX}$ = max surface area of single charged disk plate $A_{MAX} = \pi \times \left( \dfrac{C_{PANEL}}{8\epsilon_0} \right)^2$      *Equation 3c*

$A_{MAX} = \pi \times \left( \dfrac{Q_{TH}}{V_{MAX} \times 8\epsilon_0} \right)^2$      *Equation 3d*

FIG. 3

MAXIMUM RADIUS OF
SINGLE CHARGED SPHERE 4-00

$Q_{TH} = C_{PANEL} \times V_{MAX}$  *Equation 2* where:

$Q_{TH}$ = charge discharge detection threshold $C_{PANEL}$ = self-capacitance of exposed electrode panel $V_{MAX}$ = maximum preset negative voltage $C_{PANEL} = 4\epsilon_0 r_{MAX}$  *Equation 4a* where:

$r_{MAX}$ = maximum radius of single charged sphere $\epsilon_0$ = permittivity of free space, approximately $8.85 \times 10^{-12}$ F·m$^{-1}$ $r_{MAX} = \dfrac{Q_{TH}}{V_{MAX} \times 4\epsilon_0}$  *Equation 4b*

FIG. 4

UNTREATED CYLINDRICAL SAMPLE (DRY) ↙ 7A-00

|  | @ 1.0 m | @ 2.0 m |
|---|---|---|
| 45° | 455 | 50 |
| 90° | 554 | 56 |
| 135° | 644 | 26 |

FIG. 7A  Units of 1,000 NAI / $cm^3$

FIRE RETARDANT TREATED CYLINDRICAL SAMPLE ↙ 7B-00

| @ 1.0 m | dry | wet |
|---|---|---|
| 45° | 450 | 522 |
| 90° | 595 | 584 |
| 135° | 495 | 580 |

FIG. 7B  Units of 1,000 NAI / $cm^3$

WATER REPELLANT TREATED CYLINDRICAL SAMPLE ↙ 7C-00

| @ 1.0 m | dry | wet |
|---|---|---|
| 45° | 414 | 364 |
| 90° | 380 | 510 |
| 135° | 617 | 574 |

FIG. 7C  Units of 1,000 NAI / $cm^3$

CIRCULAR FIBRE BRAID SAMPLE

| @ 5 cm | @ -20 kV | | | | | @ -7 kV | | | | |
|---|---|---|---|---|---|---|---|---|---|---|
| | 0° | 90° | 180° | 270° | average | 0° | 90° | 180° | 270° | average |
| Coconut Coir | 2000 | 2000 | 2000 | 2000 | 2000 | 1500 | 300 | 1000 | 1300 | 1025 |
| Nettle (Coarse) | 2000 | 2000 | 2000 | 2000 | 2000 | 1000 | 200 | 1300 | 200 | 675 |
| Nettle (Fine) | 2000 | 2000 | 2000 | 2000 | 2000 | 98 | 650 | 900 | 1000 | 662 |
| Pineapple | 2000 | 2000 | 2000 | 2000 | 2000 | 420 | 470 | 1000 | 190 | 520 |
| Banana | 2000 | 2000 | 2000 | 2000 | 2000 | 500 | 450 | 340 | 700 | 498 |
| Jute | 2000 | 2000 | 2000 | 2000 | 2000 | 100 | 90 | 40 | 150 | 95 |
| Abaca | 2000 | 2000 | 20 | 2000 | 1375 | 2 | 20 | 33 | 55 | 28 |
| Hyacinth | 2000 | 2000 | <1 | 1500 | 1375 | 15 | <1 | <1 | <1 | 4 |

Units of 1,000 NAI / $cm^3$

FIG. 9

EXPOSED ELECTRODE NEGATIVE AIR ION DEVICE WITH FIBROUS MAT SURFACE MOUNTABLE IN AN EXPOSED ENVIRONMENT

TECHNICAL CONTRIBUTION

The present disclosure relates to negative air ion devices. More particularly, the present disclosure relates to an exposed electrode negative air ion device with fibrous mat surface that is mountable in an exposed environment.

BACKGROUND

Negative air ions (NAIs) were discovered over a hundred years ago and are widely used for air cleaning. The presence of NAIs is credited with increasing psychological health and relieving allergy symptoms. NAI emitters employ a negative voltage source with a maximum preset negative voltage in the range of −2 kV to −80 kV to elicit a corona discharge. While not required, some NAI emitter designs include a low frequency alternating current or alternating pulse characteristic in the negative voltage source.

Corona discharge is an electrical discharge caused by ionization of the air surrounding an electrode carrying a high voltage. Corona discharge represents a local region where the air has undergone electrical breakdown and has thereby become conductive, allowing negative charge to continuously leak off the electrode into the air. NAIs can include $O^-$, $O_2^-$, $O_3^-$, $CO_3^-$, $CO_4^-$, $HCO_3^-$, $NO_2^-$, and $NO_3^-$. Corona discharge occurs at locations on the electrode where the strength of the electric field (potential gradient) exceeds the dielectric strength of the air.

Ozone ions ($O_3^-$) are considered an unwanted NAI specie. Ozone production is increased when a corona discharge creates ultra-violet radiation. Ozone production can be minimized by limiting the electric field strength of the electrode. Electric field strength can be limited by lowering the maximum preset negative voltage of the electrode to around −20 kV and/or by reducing the sharpness of the electrode's point. These steps, however, also reduce the production of NAIs by the electrode. Ozone emissions can also be minimized by the presence of water, as water reacts with ozone to produce short-lived OH— radicals.

For safety reasons, early NAI emitters enclosed the NAI electrodes within an insulated housing. These early NAI emitters often included electric fans to blow the NAIs outside the housing into an exposed environment such as an apartment space or an office space. More recently, NAI emitters have been introduced that employ leaves of living house plants as an exposed electrode.

Use of living house plants as an exposed electrode, while aesthetically pleasing, can introduce the possibility of electric shock to the user. Plants, especially succulents, include large percentages of water and are therefore effective conductors. While the electric shock is not life threatening, the electric shock can startle the user and lower the user's confidence in any NAI emitter product that uses an exposed electrode.

As documented in U.S. Pat. No. 9,736,993 dated 22 Aug. 2017 entitled "Stimulating device for enhancing release of negative air ions by a plant, and plant-based negative air ion producing device" (hereafter, "the '993"), this danger of electric shock can be lessened with the use of a proximity sensor that senses the approach of a user. When the user approaches the exposed electrode in the '993 design, the device's electronics halt the output of a negative voltage source and bleed off any capacitive charge residing on the exposed electrode. In this manner, the user of the '993 design does not receive an electrical shock when touching the leaves of the house plant.

Perception of and/or reaction to (hereafter collectively referred to as "detection") an electrical current or a charge discharge has been documented in the International Electrotechnical Commission standard numbered IEC60479, part 1 and part 2, entitled "Effects of current on human beings and livestock". The IEC60479 reference documents that, as a general rule, a human body is more conductive when submitted to an alternating current compared to a direct current. An alternating current of 0.5 mA is near or at the detection threshold for frequencies in the range of 15 to 100 Hz, while a direct current does not approach the detection threshold until around 2.0 mA.

When the stored charge of a capacitor with capacitance C and a voltage V is discharged through a resistor of resistance R, the maximum (or peak) discharged current is equal to V/R. The discharged current attenuates at the rate of $e^{-t/RC}$. The RC time constant, also called tau, is equal to the product of the circuit resistance (in ohms) and the circuit capacitance (in farads). At a time RC from the start of the discharge, the voltage of the capacitor (and current through the resistor) is only about 37 percent of its maximum value. At a time of 3RC, the voltage and current are only about 5 percent of their maximum value.

For larger values of RC, the capacitive current discharge tends to affect the human body more like a direct current, as the rate of change of the voltage is lower for larger values of RC. Hence if a capacitive current discharge is passed through a higher resistance, the impact of this capacitive current discharge to the human body is more akin to a direct current (rather than an alternating current). With high resistances, the capacitive current discharge detection threshold is approximately equivalent to the direct current detection threshold (e.g., about around 2.0 mA, as discussed above). A more conservative threshold selection would be the alternating current detection threshold of 0.5 mA.

As discussed above, the maximum capacitive current discharge is equal to the maximum capacitive voltage divided by total resistance between the capacitor and ground as the electricity passes from the capacitor through the exposed electrode and the human body. The electrical resistance of the human body can be ignored in the calculations made in this disclosure as the human body has a resistance of 100 kΩ or less and the exposed electrode resistances discussed in this disclosure involve resistances larger than 1.5 MΩ. For instance, if the exposed electrode has a maximum voltage of −20 kV and the exposed electrode has a resistance of 15 MΩ, the maximum capacitive current discharge through the exposed electrode to the user will be about 1.3 mA (which is below the 2.0 mA direct current detection threshold). A proper V/R ratio can be established by matching the resistance of the exposed electrode to the maximum voltage of the exposed electrode.

The IEC60479 reference also discusses that a charge discharge (from the discharge of an electronic charge stored in the capacitance) of an exposed electrode will not be detectable to a user touching an exposed electrode if the charge discharge from the exposed electrode is 0.4 μC or less. The stored charge of a capacitor is equal to the voltage of the capacitor multiplied by the capacitance of the capacitor. A proper V·C multiple can be established by matching the capacitance of the exposed electrode to the charged voltage of the exposed electrode. E.g., a lower maximum voltage will allow a larger capacitance for the exposed electrode. The resistance of the exposed electrode does not need to be taken into account when considering the charge discharge (as only the total charge that is discharged from the exposed electrode is taken into account), however the geometric dimensions of the exposed electrode do play a key role as capacitance is a function of geometry. The self-capacitance of a single charged disk plate is $8\epsilon_0 r_D$. The self-capacitance of a single charged sphere is $4\epsilon_0 r_D$. Thus, for a given maximum preset negative voltage, the maximum charge transfer from the charge discharge of an exposed electrode (whether a disk plate electrode or a spherical electrode) can be adjusted by limiting the geometric size of the exposed electrode.

As detailed in the IEC60479 reference, the detection threshold for a current or a charge discharge depends on several parameters, such as the area of the body in contact with an electrode (contact area), the conditions of contact (e.g., dry, wet, pressure, temperature), and also on the physiological characteristics of the individual. Detection thresholds are not the same for all humans and are not the same for all operational conditions. Repeated experience with the environment or consumer product may lead to a human ignoring an otherwise detectable currents or charge discharge in that environment or from that consumer product.

Application of the findings of IEC60479 reference to existing consumer electronic products can be found in "Design Guideline for Developing Safe Systems that Apply Electricity to the Human Body", by MICHINARI KONO, et al., published by ACM Transactions on Computer-Human Interaction, Vol. 25, No. 3, Article 19, published June 2018 (hereafter, "the Kono article"). The Kono article provides over twenty examples of the application of small electrical charges and current to the human body via the design of the consumer electronic product's electronics and its external user interface. Example applications include the capacitive user interface display of a smart phone's touch screen. The small electrical charges and currents for each of the listed consumer electronic products are typically below the level of human detection (e.g., see Table 1 on page 19:12 of the Kono article).

Similar to the consumer electronics listed in the Kono article, NAI emitters with exposed electrodes can benefit from adhering to the teachings of the IEC60479 reference. While the '993 addresses the issue of electric shock, its solution is to turn off the NAI emitter's power and ground the exposed electrode. The '993 design is not practical for exposed electrodes that are located in heavy user traffic areas because the proximity sensor would likely shut down the NAI emitter on a nearly continuous basis. Also, if an occupant of the high use traffic area is not familiar with the '993 design, the occupant could inadvertently encounter a detectable electric shock due to inexperience with the '993 design (such as by touching the exposed electrode while located outside the sensing angle of the proximity sensor).

Therefore, what is needed is an NAI emitter with an exposed electrode that may remain in continuous operation in an exposed environment despite the location of users or the behavior of users located within touching distance of the exposed electrode.

SUMMARY

In its most general form, the invention is an exposed electrode negative air ion device, either stand-alone or mounted in an exposed environment 56 as part of a negative air ion panel system 50. Each device comprises: (a) an electronics module 22, the electronics module 22 including a negative voltage generator 22B; and (b) an exposed electrode 10, the exposed electrode 10 including a mat surface 11 of intertwined individual fibres electrically connected to the negative voltage generator 22B. The mat surface 11 has a minimum mean resistance of $R_{MIN}$ to restrict a maximum capacitive current discharge below a capacitive current discharge detection threshold. The negative voltage generator 22B is configured to generate a negative voltage source 23 from a power supply 21 within a set of electrical parameters. The set of electrical parameters includes a maximum preset negative voltage of Vi and a maximum operating current, the maximum operating current set below or equal to a direct current detection threshold.

In more detail, a first embodiment of the invention is an exposed electrode negative air ion device, the device comprising: (a) an electronics module including an input port, a negative voltage generator, and an output port; and (b) an exposed electrode, the exposed electrode including a mat surface of intertwined individual fibres. The input port is configured to electrically receive a power supply and electrically route the power supply to the negative voltage generator. The negative voltage generator is configured to: (1) generate a negative voltage source from the power supply; and (2) output the negative voltage source to the output port within a set of electrical parameters. The set of electrical parameters includes: (1) a maximum preset negative voltage of $V_{MAX}$; and (2) a maximum operating current, the maximum operating current set below or equal to a direct current detection threshold. The mat surface of the exposed electrode is directly or indirectly electrically connected to the output port of the electronics module at one or more electrical connection points.

In the first embodiment of the invention, the mat surface has a minimum mean resistance of $R_{MIN}$, as measured during a discharge event between the output port of the electronics module and a measurement probe, the measurement probe tipped with a polished stainless steel sphere having a diameter of twenty millimetres, where:

$$R_{MIN} = \frac{V_{MAX}}{I_{TH}}; \qquad \text{(Equation 1)}$$

and $I_{TH}$ is a capacitive current discharge detection threshold.

A second embodiment of the invention is a negative air ion panel system comprising two or more of the device of the first embodiment of the invention and the alternative embodiments of the first embodiment of the invention.

In an alternative embodiment of the second embodiment of the invention, each of the mat surfaces of the devices in the system are configured in at least one of: (a) a grid arrangement on a wall, a ceiling, or a floor of the exposed environment; (b) a grouping of spheres or cylinders in the exposed environment; and (c) a set of individual panel mountings in the exposed environment. Note that use of the invention is not limited to the configurations listed in this alternative embodiment; non-limiting examples for configuration of the mat surfaces include their mounting: (a) outdoors to trees, overhead covered walkways, bus shelters, lamp posts, street furniture, and advertising panels; and (b) indoors on cubicle walls, lamp shades, sun shades, and furniture sidings.

In an alternative embodiment of the second embodiment of the invention, the system further comprising a gateway, a network, and an offsite server, wherein each electronics module of the devices in the system further includes an IoT module in data communication with the offsite server through the gateway and the network.

BRIEF DESCRIPTION OF THE DRAWINGS

Embodiments of the present disclosure are described herein with reference to the drawings in which:

FIG. 3 lists a series of equations representing the derivation of an equation for the maximum permissible surface area of a single charged disk plate at a given voltage.

FIG. 4 lists a series of equations representing the derivation of an equation for the maximum permissible radius of a single charged sphere at a given voltage.

FIG. 7A-7C are charts documenting test data collection values for cylindrical samples of coconut coir with various pre-treatments.

FIG. 9 is a chart documenting test data collection values for circular samples of various types of fibre braids.

DETAILED DESCRIPTION

In the following detailed description, reference is made to the accompanying drawings, which form a part hereof. The illustrative embodiments described in the detailed description, drawings and claims are not meant to be limiting. Other embodiments can be utilized, and other changes can be made, without departing from the spirit or scope of the subject matter presented herein. Unless specified otherwise, the terms "comprising," "comprise," "including" and "include" used herein, and grammatical variants thereof, are intended to represent "open" or "inclusive" language such that they include recited elements but also permit inclusion of additional, un-recited elements. As used herein, the software and hardware of a "server" may be implemented within: a single stand-alone computer, a stand-alone server, multiple dedicated servers, and/or a virtual server running on a larger network of servers and/or a cloud-based service.

Figure 1:
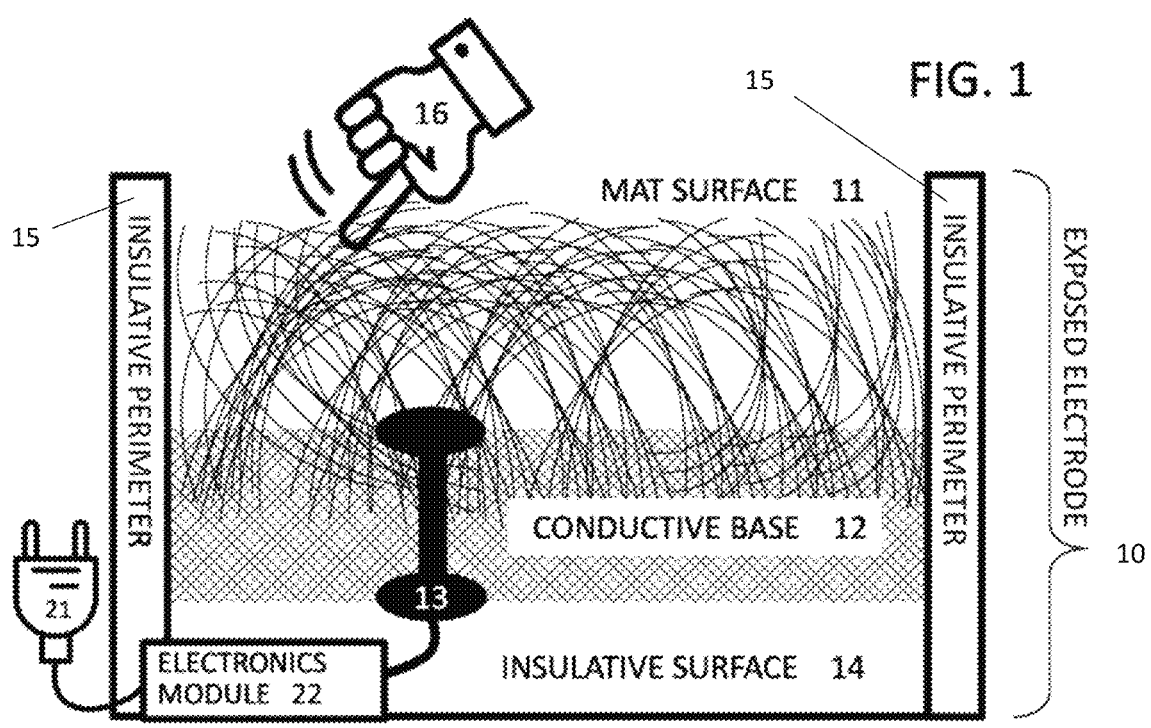
FIG. 1 is a block diagram representing an exposed electrode with an integrated electronics module and a conductive base in an embodiment of the invention.

FIG. 1 is a block diagram representing an exposed electrode 10 with an integrated electronics module 22 and a conductive base 12 in an embodiment of the invention. The conductive base 12 is located between a mat surface 11 and an insulative surface 14. The mat surface 11 is comprised of intertwined individual fibres. As illustrated in FIG. 1, the proximate ends of the intertwined individual fibres are embedded inside the conductive base 12; the distal ends of the intertwined individual fibres extend toward the mat surface 11 (see below for examples of alternative electrical connection means between the intertwined individual fibres and the electronics module 22). The exposed electrode 10 includes an insulative perimeter 15. The electronics module 22 is in electrical connection to the power supply 21. The electronics module 22 is in electrical connection to an electrical connection point 13 rivet piercing the conductive base 12.

In FIG. 1, the possible user contact with the mat surface 11 is depicted at an extended finger 16. The mat surface 11 has a minimum mean resistance of $R_{MIN}$, as measured during a discharge event between the output port 22C of the electronics module 22 and a measurement probe, the measurement probe tipped with a polished stainless steel sphere having a diameter of twenty millimetres, where:

$$R_{MIN} = \frac{V_{MAX}}{I_{TH}};$$ (Equation 1)

and $I_{TH}$ is a capacitive current discharge detection threshold.

Under Equation 1, if the maximum preset negative voltage of $V_{MAX}$ is −20 kV and the capacitive current discharge detection threshold is 2 mA, then the calculated minimum mean resistance of $R_{MIN}$ would be 10 ma Maximum preset negative voltage of $V_{MAX}$ values of −40 kV, −60 kV, and −80 kV result in the minimum mean resistance of $R_{MIN}$ calculations of 20 MΩ, 30 MΩ, and 40 MΩ, respectively, if the capacitive current discharge detection threshold is 2 mA. As −20 kV is one of the more optimal voltages for the maximum preset negative voltage of $V_{MAX}$ and −80 kV is one of the highest likely voltages for the maximum negative preset voltage of $V_{MAX}$, a preferable range for minimum mean resistance of $R_{MIN}$ is from 10 MΩ to 40 MΩ, if the capacitive current discharge detection threshold is 2 mA.

For some low voltage exposed electrode negative air ion device embodiments, a lower maximum preset negative voltage of $V_{MAX}$ could be set in the range of −3 kV to −20 kV, resulting in an acceptable range for minimum mean resistance of $R_{MIN}$ from 1.5 MΩ to 10 MΩ, if the capacitive current discharge detection threshold is 2 mA. The lowest practical value for the maximum preset negative voltage of $V_{MAX}$ about −3 kV, as below this voltage threshold there is very little corona discharge. See FIGS. 8 and 9 for experimental data taken at −7 kV and −20 kV for the maximum preset negative voltage of Vim.

Higher voltages values for maximum preset negative voltage of $V_{MAX}$ require increasingly larger creepage and clearance distances in the design of the exposed electrode 10. Hence higher values of the maximum preset negative voltage of $V_{MAX}$ require a more bulky design for the exposed electrode 10 without changing its basic functionality. For many indoor installations, an upper limit of about −40 kV is preferable due to practical limitations in creepage and clearance distances.

For each of these values of the maximum preset negative voltage of $V_{MAX}$, the invention prevents user discomfort from any electrical discharge when the exposed electrode negative air ion device properly pairs a maximum preset voltage of $V_{MAX}$ range to the minimum mean resistance of RA/HA/of the mat surface 11, according to Equation 1.

While under most circumstances a capacitive current discharge tends to affect the human body more like a direct current, some users' detection of a capacitive current discharge may be more akin to the users' detection of an alternating current. An alternating current of 0.5 mA is near or at the detection threshold for alternating currents of frequencies in the range of 15 to 100 Hz, while a direct current does not approach the detection threshold until around 2.0 mA. Thus for added protection of the user, the capacitive current discharge detection threshold could be set at 0.5 mA. Using a capacitive current discharge detection threshold of 0.5 mA, the minimum mean resistance of $R_{MIN}$ should be increased fourfold. E.g., under Equation 1, the maximum preset negative voltage of $V_{MAX}$ values of −3 kV, 20 kV and −40 kV result in the minimum mean resistance of R MIN calculations of 6 MΩ, 40 MΩ, and 80 MΩ, respectively if using a capacitive current discharge detection threshold of 0.5 mA.

The minimum mean resistance of $R_{MIN}$, as defined above in Equation 1, is measured during a discharge event, sometimes referred to as an electric shock. A discharge event is an abrupt electrical discharge, such as from the mat surface 11 to an extended finger 16, that occurs when a sufficiently high electric field creates an ionized, electrically conductive channel through the normally-insulating air. The measurement of the minimum mean resistance of $R_{MIN}$ during a discharge event best mimics the intended technical benefit of the invention during operating conditions. E.g., if the resistance were measured outside of a discharge event, the resistance measured by the measurement probe would be far higher than during a discharge event.

For a given voltage, a measurement probe tipped with a sphere creates a lower magnitude electric field than a measurement probe with a sharp point. The measurement probe used to measure minimum mean resistance of $R_{MIN}$ is tipped with a polished stainless steel sphere having a diameter of twenty millimetres to best approximate a user touching the mat surface 11 with an extended finger 16. In practice, the sphere can be a stainless steel machine ball knob attached to the body of the measurement probe with an M5 screw.

The minimum mean resistance of $R_{MIN}$ is a "mean" resistance, as variations in the mat surface 11 may result in higher or lower resistance measurements at various locations of the mat surface 11. A minimum mean resistance of $R_{MIN}$ of a rectangular mat surface 11 could be, for instance, the fifth highest resistance measured among a square grid of nine locations on the mat surface 11, where the square grid has three rows and three columns. A minimum mean resistance of $R_{MIN}$ of a spherical mat surface 11 could be, for instance, the third highest resistance measured among a first point at the sphere's pole opposite the electrical connection point 13 and four additional points along the equator of the sphere at 0°, 90°, 180°, and 270° (the electrical connection point 13 and the first point defining the axis of the sphere).

As depicted in FIG. 1, the electrical connection point 13 employs a conductive rivet that pierces through the conductive base 12. The conductive base 12 can be pierced with multiple conductive rivets at various locations of the conductive base 12, wherein each conductive rivet is connected to the electronics module 22 via electrical wiring. Other electrical connection means such as conducting screws, flat surface electrodes, conductive epoxy, electrical wiring, or a combination thereof can also be employed at the one or more electrical connection points 13.

As depicted in FIG. 1, the proximate ends of the intertwined individual fibres are embedded within the conductive base 12, however other methods of mounting the intertwined individual fibres on the conductive base 12 (such as with a conductive epoxy, heat treatment, weave, or mechanical pressure) are also possible. The mat surface 11 of the intertwined individual fibres can be either permanently attached to the conductive base 12 or the mat surface 11 can be replaceable.

As depicted in FIG. 1, the electronics module 22 is integrated into the exposed electrode 10, however the electronics module 22 can also be mounted outside the exposed electrode 10. E.g., the exposed electrode 10 could be a replaceable unit that snaps into place on a mounted bracket housing one or more devices, where the mounting bracket includes the electronics module(s) 22. Also, multiple exposed electrodes 10 could route to different output ports 22C of a single electronics module 22.

As depicted in FIG. 1, the exposed electrode 10 includes a conductive base 12 and the negative voltage source 23 passes from the output port 22C, to the conductive base 12 at an electrical connection point 13, and the mat surface of intertwined individual fibres 11. However, in other embodiments of the invention, the conductive base 12 is not included in the exposed electrode 10; the negative voltage source 23 passes from the output port 22C to the mat surface of intertwined individual fibres 11 at one or more electrical connection points 13. In this embodiment, the intertwined individual fibres at the one or more electrical connection points 13 act as conductors to distribute the negative voltage source 23 across the mat surface 11.

Figure 2:
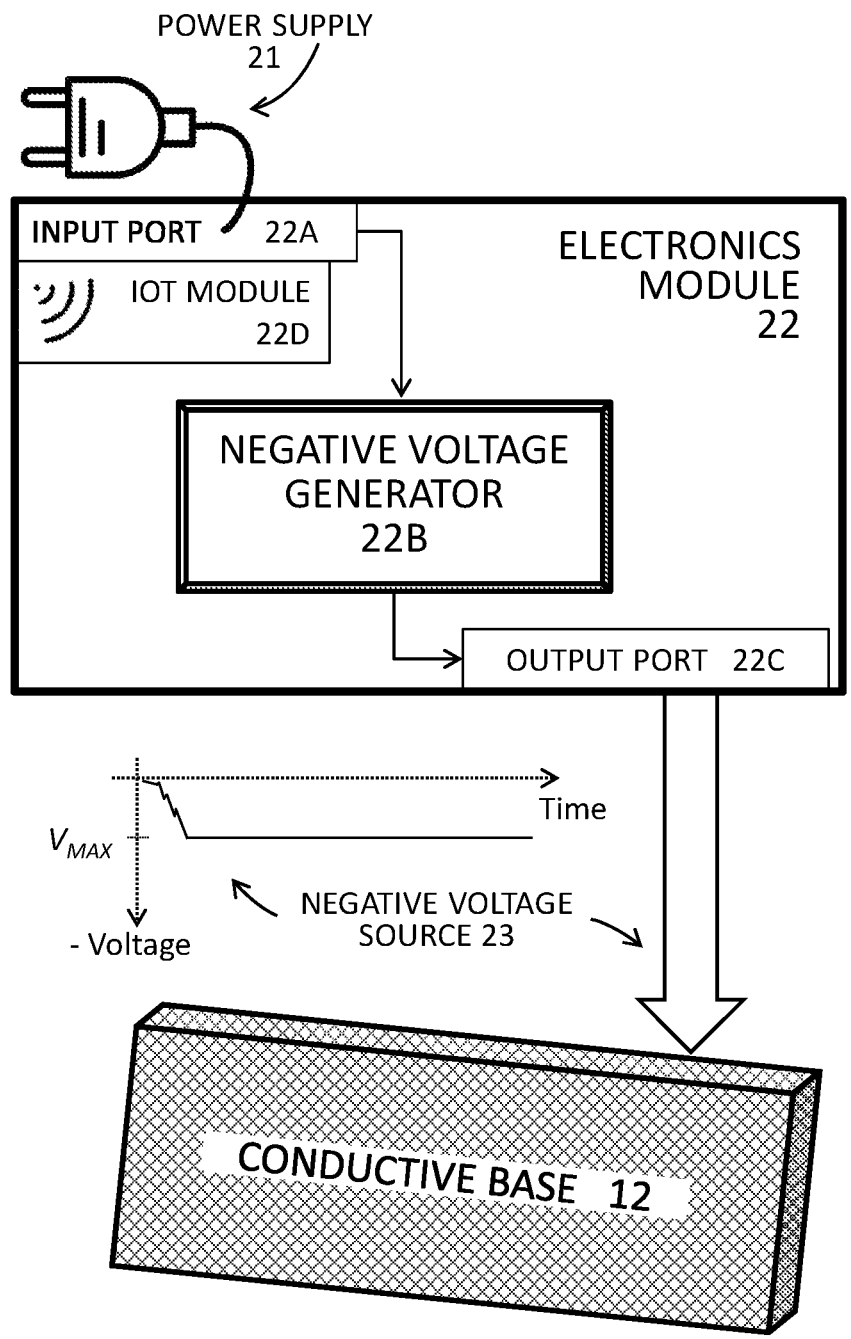
FIG. 2 is a block diagram representing the output of a negative voltage source from an electronics module to the conductive base in an embodiment of the invention.

FIG. 2 is a block diagram representing the output of a negative voltage source 23 from an output port 22C of the electronics module 22 to the conductive base 12 of the exposed electrode 10 in an embodiment of the invention. The electronics module 22 includes an input port 22A in electrical connection to a power supply 21 and an output port 22C in electrical connection to the conductive base 12 of an exposed electrode 10 (not shown). The electronics module 22 includes a negative voltage generator 22B configured to produce a negative voltage source 23 with a maximum preset negative voltage of Vex.

As depicted in FIG. 2, the electronics module 22 includes an IoT module 22D with wireless communication capability. The IoT module 22D can also employ wired powerline communication through the power supply's 21 wire connections. See the description of FIG. 5 below for more details on the use of the IoT modules 22D in the negative air ion panel system 50.

As depicted in FIG. 2, the negative voltage source 23 passes from the output port 22C, of the electronics module 22 to the conductive base 12. However, in other embodiments of the invention, the conductive base 12 is not included and the negative voltage source 23 passes from the output port 22C to the mat surface of intertwined individual fibres 11 at one or more electrical connection points 13. In this embodiment, the intertwined individual fibres at the one or more electrical connection points 13 act as conductors to distribute the negative voltage source 23 across the mat surface 11.

FIG. 3 lists a series of equations 3-00 representing the derivation of an equation for the maximum permissible surface area $A_{MAX}$ of a single charged disk plate at a given voltage in an embodiment of the invention. In alternative embodiments of the invention, the user's detection of a shock can be eliminated by limiting the maximum capacitance of the exposed electrode 10, given a maximum preset negative voltage. Capacitance is a function of the geometry of the capacitor. A single charged disk plate has a self-capacitance of $8\epsilon_0 r_D$ per Equation 3a of FIG. 3. The self-capacitance of a flat mat surface 11 of an exposed electrode 10 (such as a rectangular-shaped panel) can be roughly approximated by the self-capacitance of a single charged disk plate of identical surface area.

As discussed in the IEC60479 reference, the charge discharge detection threshold of a human is 0.4 μC. The maximum charge of a capacitor is its capacitance times the capacitor's voltage (here the maximum preset negative voltage of Vex). $V_{MAX}$ is, from experimental data, preferably about −20 kV (e.g., in the range of −18 kV to −22 kV) to efficiently create NAIs. Assuming a −20 kV Vex, then the approximate capacitance of a rectangular-shaped panel should be limited to 20 pF per Equation 2 of FIG. 3 if the charge discharge detection threshold $Q_{TH}$ is 0.4 µC. As derived in the equations of FIG. 3, the maximum surface area of a single charged disk plate $A_{MAX}$ is represented by Equations 3b to 3d.

Employing Equation 3c, the maximum surface area $A_{MAX}$ of a disk-shaped panel would be 0.25 square metres. E.g., to limit the maximum charge stored on the disk-shaped panel to 0.4 µC (the charge discharge detection threshold of a human) with a −20 kV $V_{MAX}$, the capacitance must be limited to 20 pF by limiting the surface area of the panel to about 0.25 square metres. Note that the maximum surface area, per Equation 3d, is proportional to $V_{MAX}^{-2}$; if $V_{MAX}$ is doubled to −40 kV then the maximum surface of the maximum surface area of the mat surface 11 of a disk-shaped panel should be reduced by 75% (e.g., for the above example, from 0.25 square metres to 0.0625 square metres). The Equation 3c calculation for the self-capacitance of a disk-shaped panel can be used to approximate the maximum surface area $A_{MAX}$ of a rectangular-shaped panel mat surface 11 or any other mat surface 11 that is flat in shape. E.g., as used in this disclosure and the claims, the maximum surface area $A_{MAX}$ is used to approximate a maximum surface area for any type of flat surface (whether disk-shaped or rectangular-shaped).

FIG. 4 lists a series of equations 4-00 representing the derivation of an equation for the maximum permissible radius of a single charged sphere at a given voltage in an embodiment of the invention. As in the case of a rectangular-shaped panel geometry discussed above in regard to FIG. 3, the user's detection of a shock can be eliminated by limiting the capacitance of a sphere-shaped exposed electrode 10 at a given maximum preset negative voltage. The self-capacitance of a sphere-shaped exposed electrode 10 can be roughly approximated by the self-capacitance of a single charged sphere. A single charged sphere has the self-capacitance of $4\epsilon_0 r_D$ per Equation 4a of FIG. 4.

Assuming a −20 kV Vex and a charge discharge detection threshold of 0.4 µC, the capacitance of an exposed electrode 10 should be limited to 20 pF per Equation 2 of FIG. 4. As derived in the equations of FIG. 4, the maximum radius of a single charged sphere is represented by Equation 4b. Employing Equation 4b, the maximum radius of the spherical electrode can be roughly approximated as 0.56 metres so as to limit the capacitance to 20 pF. Note that the maximum radius of the sphere, per Equation 4b, is proportional to $V_{MAX}^{-1}$; if $V_{MAX}$ is doubled to −40 kV then the maximum radius of a sphere-shaped panel is reduced by 50% to approximately 0.28 metres.

Figure 5:
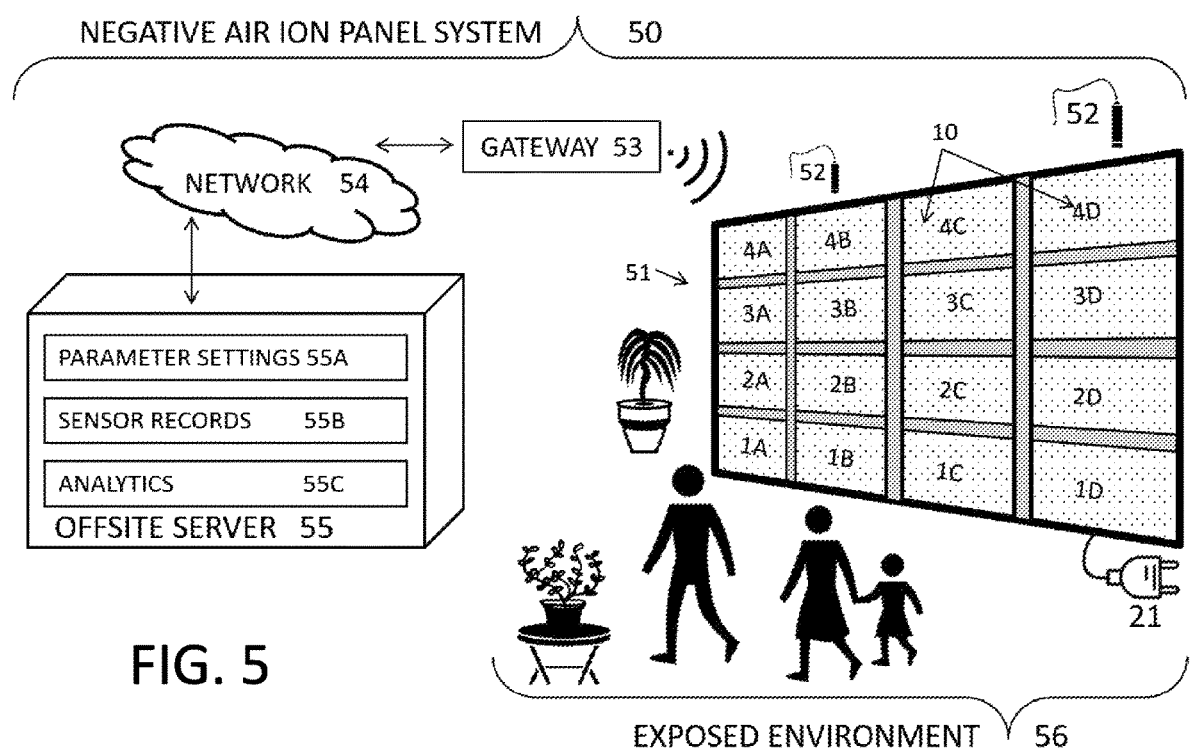
FIG. 5 is a block diagram representing a negative air ion panel system in an embodiment of the invention.

FIG. 5 is a block diagram representing a negative air ion panel system 50 in an embodiment of the invention. The system 50 includes a grid arrangement 51 on a wall with four columns and four rows of exposed electrodes 10 (see items 1A to 1D, 2A to 2D, 3A to 3D, and 4A to 4D) in an exposed environment 56. The grid arrangement 51 is electrically connected to a power supply 21. FIG. 5 illustrates an exposed environment 56 in which humans are present; in the exposed environment 56 the humans are not insulated or prevented from touching the mat surfaces 11 of the exposed electrodes 10.

As illustrated in FIG. 5, the exposed environment 56 also includes a gateway 53 with wireless data communication capability to a plurality of sensors 52 mounted in the exposed environment 56. Though not illustrated in FIG. 5, the gateway 53 can also connect wirelessly to the IoT modules 22D of each device or via wired powerline communication. The gateway 53 is in data communication with a network 54, and the network 54 of the system 50 is connected to an offsite server 55. The offsite server 55 includes a parameter settings module 55A, a sensor records module 55B, and an analytics module 55C.

Figure 6:
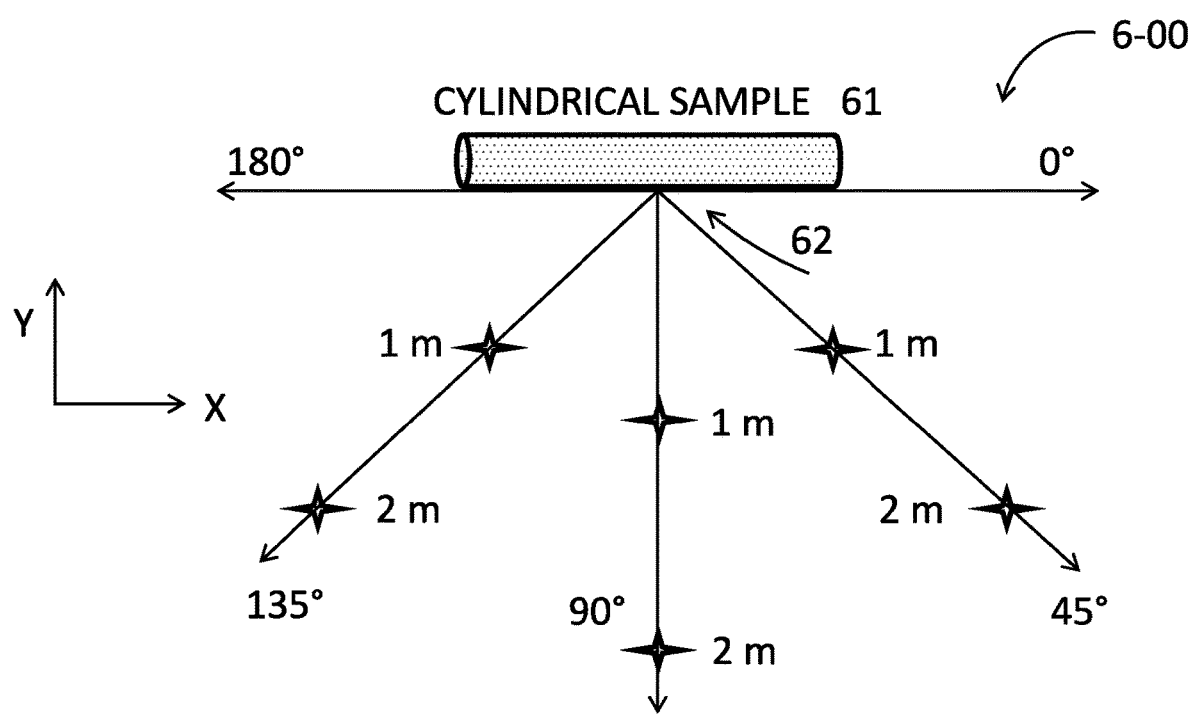
FIG. 6 is a diagram identifying test data collection locations for the testing of various cylindrical samples.

FIG. 6 includes a diagram 6-00 identifying test data collection locations for the testing of various cylindrical samples 61. The test data was collected variously at one metre or two metres from an outside center 62 of the cylindrical sample 61 at the identified angles of 45°, 90°, and 135° in the x-y plane parallel to the floor as illustrated in diagram 6-00.

FIG. 7A-7C are charts (7A-00, 7B-00, and 7C-00) documenting test data values experimentally collected for various cylindrical samples 61 of intertwined individual fibres wrapped around a cylindrical pole and electrically connected to a voltage pulse source. The test data summarized in the charts (7A-00, 7B-00, and 7C-00) represents average negative air ion readings over a sample time of about 10 seconds. The charts' test data are provided in units of 1,000 negative ions per cubic centimetre (1,000 NAI/cm$^3$).

The FIG. 7A chart 7A-00 provides test data taken at one metre and at two metres from the outside center 62 of the cylindrical sample 61, as illustrated in the diagram 6-00 of FIG. 6. The FIG. 7B chart 7B-00 and the FIG. 7C chart 7C-00 provide test data taken at one metre from the outside center 62 of the cylindrical sample 61, as illustrated in the diagram 6-00 of FIG. 6. The ambient NAI during the collection of test data was approximately 130 NAI/cm$^3$. The test data represents the average negative ion emissions readings over a sample time of about 10 seconds. The maximum preset negative voltage for the set of negative voltage pulses was −20 kV.

The chart 7A-00 of FIG. 7A provides test data for a cylindrical coconut coir sample that has not been treated with a fire retardant and has not been treated with a water repellant. The chart 7B-00 of FIG. 7B provides test data for a cylindrical coconut coir sample that has been treated with a fire retardant. The chart 7C-00 of FIG. 7C provides test data for a cylindrical coconut coir sample that has been treated with a water repellant.

The chart 7A-00 of FIG. 7A demonstrates the decrease in NAI concentration as a function of distance from the outside center 62 of the cylindrical sample 61. A comparison of the test data of the three charts (7A-00, 7B-00, and 7C-00) indicates that: (i) NAI emissions for coconut coir fibres is about the same for untreated, fire retardant treated, and water repellant treated coconut coir; and (ii) whether wet or dry, coconut coir fibres emit about the same NAI concentrations.

Figure 8:
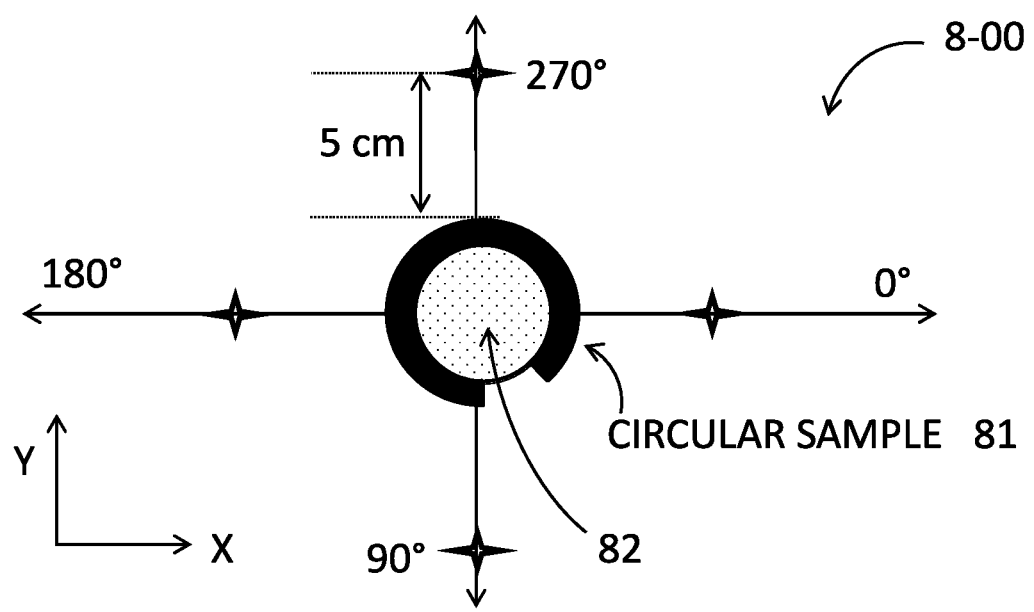
FIG. 8 is a diagram identifying test data collection locations for the testing of various circular samples.

FIG. 8 includes a diagram 8-00 identifying test data collection locations for the testing of circular samples 81 in an x-y plane parallel to the floor. The circular samples 81 were electrically connected to a voltage pulse source. The circular samples 81 of various fibre braids were: (i) approximately 20 centimetres in length; and (ii) wrapped around and attached to the equator area of a sphere-shaped ball 82. The test data was collected as illustrated in diagram 8-00: (i) at a radial distance of 5 cm from the braid at the identified angles of 90°, 180°, and 270°; and (ii) in the x-y plane parallel to the floor.

The chart 9-00 of FIG. 9 documents test data values experimentally collected for various types of circular samples 81 for fibre braids. The length of each fibre braid was approximately 20 centimetres. The test data summarized in the chart 9-00 represents the average negative ion emissions readings over a sample time of about 10 seconds at a radial distance of 5 centimetres from the surface of each of the circular samples of fibre braid. The chart's test data is provided in units of 1,000 negative ions per cubic centimetre (1,000 NAI/cm$^3$). The ambient NAI during the collection of test data was approximately 130 NAI/cm$^3$. Test data was taken with the maximum preset negative voltage for the set of negative voltage pulses at −20 kV and separately at −7 kV. Sample braids included fibres from coconut coir, nettle (coarse), nettle (fine), pineapple, banana, jut, abaca, and hyacinth.

As documented in chart 9-00, the test data documents that NM emissions significantly improved with the maximum preset negative voltage set at −20 kV, as contrasted with −7 kV. The test data also demonstrates that NAI emissions were generally consistent along at each angle tested in the x-y plane. Overall, coconut coir and coarse nettle braids tested better than the other fibre types. It is theorized that the spiky or furry nature of natural fibres such as coconut coir provides a high NAI emission efficacy over an extended surface area because the uneven surface and sharp end points of the individual fibres provide a large number of locations for high curvature geometric shapes, resulting in a large number of local electrical field maximums that separately facilitate corona discharge.

A first embodiment of the invention is an exposed electrode 10 negative air ion device, the device comprising: (a) an electronics module 22 including an input port 22A, a negative voltage generator 22B, and an output port 22C; and (b) an exposed electrode the exposed electrode 10 including a mat surface 11 of intertwined individual fibres. The input port 22A is configured to electrically receive a power supply 21 and electrically route the power supply 21 to the negative voltage generator 22B. The negative voltage generator 22B is configured to: (1) generate a negative voltage source from the power supply 21; and (2) output the negative voltage source to the output port 22C within a set of electrical parameters. The set of electrical parameters includes: (1) a maximum preset negative voltage of VAN; and (2) a maximum operating current, the maximum operating current set below or equal to a direct current detection threshold. The mat surface 11 of the exposed electrode 10 is directly or indirectly electrically connected to the output port 22C of the electronics module 22 at one or more electrical connection points 13. The mat surface 11 has a minimum mean resistance of $R_{MIN}$, as measured during a discharge event between the output port 22C of the electronics module 22 and a measurement probe, the measurement probe tipped with a polished stainless steel sphere having a diameter of twenty millimetres, where:

$$R_{MIN} = \frac{V_{MAX}}{I_{TH}}; \qquad \text{(Equation 1)}$$

and $I_{TH}$ is a capacitive current discharge detection threshold.

In an alternate embodiment of the first embodiment of the invention, the mat surface 11 is flat in shape and has a maximum surface area of $A_{MAX}$, where:

$$A_{MAX} = \pi \times \left(\frac{Q_{TH}}{V_{MAX} \times 8\epsilon_0}\right)^2; \qquad \text{(Equation 3d)}$$

$Q_{TH}$ is a charge discharge detection threshold; and $\epsilon_0$ is permittivity of free space.

The charge discharge detection threshold can be 0.4 µC.

In an alternate embodiment of the first embodiment of the invention, the mat surface 11 is spherical in shape and has a maximum radius of $r_{MAX}$, where:

$$r_{MAX} = \frac{Q_{TH}}{V_{MAX} \times 4\epsilon_0}; \qquad \text{(Equation 4b)}$$

$Q_{TH}$ is a charge discharge detection threshold; and $\epsilon_0$ is permittivity of free space.

The charge discharge detection threshold can be 0.4 µC.

In an alternate embodiment of the first embodiment of the invention, the direct current detection threshold is 2.0 mA.

In an alternate embodiment of the first embodiment of the invention, the capacitive current discharge detection threshold is 2.0 mA.

In an alternate embodiment of the first embodiment of the invention, the minimum mean resistance of $R_{MIN}$ is in the range of 10 MΩ to 40 MΩ. Note that the invention is not limited to the minimum mean resistance of $R_{MIN}$ range dictated by this alternative embodiment; the full minimum mean resistance of $R_{MIN}$ range is 1.5 MΩ to 80 MΩ.

In an alternate embodiment of the first embodiment of the invention, the intertwined individual fibres are comprised of at least one of coconut coir fibre, hyacinth fibre, jute fibre, abaca fibre, banana fibre, pineapple fibre, and nettle fibre. Note that the invention is not limited to the natural fibres listed in this alternative embodiment; alternative natural fibres can also be used with the invention, and, additionally, engineered polymer fibres may also be used with the invention.

In an alternate embodiment of the first embodiment of the invention, the intertwined individual fibres are comprised of flame retardant coconut coir fibres with: (a) a mean diameter in the range of 0.1 mm to 0.5 mm; and (b) a mean length in the range of 0.15 m to 0.28 m.

In an alternate embodiment of the first embodiment of the invention, the intertwined individual fibres are hygroscopic. Hygroscopicity of the natural fibres is an important characteristic of natural fibres because the water content of natural fibres is the primary conductive material of the fibre. Without this water within the fibre, natural fibres would be unsuitable for NAI generation because the resistance of the fibres would be excessively high. The main components of plant fibres are, in decreasing order of hygroscopicity: hemicellulose, cellulose, and lignin. By selecting fibres with different ratios of these three constituents, it is possible to tune the bulk resistivity of a fibrous mat surface 11 of an exposed electrode 10 for a particular humidity.

Additionally, hygroscopic fibres have the benefit of potentially reducing ozone emissions as water reacts with ozone to produce short live OH$^-$ radicals. Natural fibres have high levels of hygroscopicity. Certain engineered polymers fibres are also hygroscopic. Hygroscopic engineered polymer fibres include nylon, ABS, polycarbonate, cellulose, and poly(methyl methacrylate). Engineered polymer fibres can also be coated to increase their hygroscopicity (e.g., see Japanese Patent No. 3177719B2 entitled "Synthetic fiber with improved hygroscopicity" granted 18 Jun. 2001).

In an alternate embodiment of the first embodiment of the invention, the mat surface 11 of the exposed electrode 10 is at least one of: (a) a length of intertwined individual fibres wrapped around a spherical base or a cylindrical base; (b) a suspended rope; and (c) a rectangular mat.

In an alternate embodiment of the first embodiment of the invention, the maximum preset negative voltage of $V_{MAX}$ ranges from −18 kV to −22 kV. Use of a maximum preset negative voltage in this range has the benefit of reducing the production of ozone ions while maintaining an effective generation of negative air ions. Note that the invention is not limited to the maximum preset negative voltage range dictated by this alternative embodiment; the full maximum preset negative voltage of $V_{MAX}$ ranges from −3 kV to 80 kV.

In an alternate embodiment of the first embodiment of the invention, the electronics module 22 is incorporated into the exposed electrode 10.

In an alternate embodiment of the first embodiment of the invention: (a) the exposed electrode 10 includes a conductive base 12; (b) the mat surface 11 of intertwined individual fibres is mounted on the conductive base 12; and (c) conductive base 12 is electrically connected to the output port 22C of the electronics module 22 at one or more electrical connection points 13. This embodiment can alternatively be configured such that: (a) the exposed electrode 10 includes an insulative perimeter 15 and an insulative surface 14; and (b) the conductive base 12 is located between the mat surface 11 and the insulative surface 14. This embodiment can also alternatively be configured such that the conductive base 12 comprises a carbon infused elastomer.

A second embodiment of the invention is a negative air ion panel system 50 comprising two or more of the device of the first embodiment of the invention and/or the alternative embodiments of the first embodiment of the invention.

In an alternative embodiment of the second embodiment of the invention, each of the mat surfaces 11 of the devices in the system 50 are configured in at least one of: (a) a grid arrangement 51 on a wall, a ceiling, or a floor of the exposed environment 56; (b) a grouping of spheres or cylinders in the exposed environment 56; and (c) a set of individual panel mountings in the exposed environment 56. Note that use of the invention is not limited to the configurations listed in this alternative embodiment; non-limiting examples for configuration of the mat surfaces 11 include their mounting: (a) outdoors to trees, overhead covered walkways, bus shelters, lamp posts, street furniture, and advertising panels; and (b) indoors on cubicle walls, lamp shades, sun shades, and furniture sidings.

In an alternative embodiment of the second embodiment of the invention, the power supply 21 of each device is generated by a local solar panel.

In an alternative embodiment of the second embodiment of the invention, the system 50 further comprising a gateway 53, a network 54, and an offsite server 55, wherein each electronics module 22 of the devices in the system 50 further includes an IoT module 22D in data communication with the offsite server 55 through the gateway 53 and the network 54. This embodiment can alternatively be configured such that: (a) the offsite server 55 further comprises a parameter settings module 55A, the parameter settings module 55A configured to store a latest set of electrical parameters for each device in the system 50; (b) the IoT module 22D of each device is configured for wired or wireless data communication to and from the parameter settings module 55A of the offsite server via the gateway 53 and the network 54; (c) the parameter settings module 55A is configured to send each device the latest set of electrical parameters for the device; and (d) each device is configured to receive the latest set of electrical parameters for the device, via the IoT module 22D of the device, from the parameter settings module 55A. This embodiment can alternatively be configured such that: (a) the offsite server 55 further comprises a sensor records module 55B; (b) the system 50 further comprises a plurality of sensors 52 mounted in the exposed environment 56 that are each in data communication with the sensor records module 55B of the offsite server 55 via the gateway 53 and the network 54; and (c) the sensors 52 include at least one of a temperature sensor 52, a humidity sensor 52, a motion sensor 52; and a negative ion concentration sensor 52. This embodiment can alternatively be configured such that: (a) the offsite server 55 further comprises an analytics module 55C; and (b) the analytics module 55C is configured to create a system 50 report detailing at least one of a history of selected sensor 52 data stored in the sensor records module 55B and a summary of the latest set of electrical parameters for each device in the system 50.

The primary technical solution of the invention maintaining current levels and/or charge discharge levels below the detection threshold. The maximum operating current is set below or equal to the direct current detection threshold by the electronics module 22. The maximum capacitive current discharge is maintained below or equal to a capacitive current discharge detection threshold with: (i) the use of high resistance intertwined individual fibres on the mat surface 11 of the exposed electrode 10 that maintain at least a minimum mean resistance of R MIN over the mat surface 11; and (ii) a maximum preset negative voltage that is matched to the minimum mean resistance of $R_{MIN}$ of the mat surface 11. In alternative embodiments, the maximum charge discharge can additionally be maintained below or equal to a charge discharge detection threshold by limiting the capacitance of a flat exposed electrode 10 via a limitation of the maximum surface area of $A_{MAX}$ or by limiting the capacitance of spherical exposed electrode 10 via the maximum radius of $r_{MAX}$.

The result of limiting these current and charge discharge characteristics is an exposed electrode 10 negative air ion device with an exposed electrode 10 that can be touched by a user in an exposed environment 56 without physical pain and/or discomfort from any current or charge discharge. This design permits continuous and safe operation of the exposed electrode negative air ion device in an exposed environment 56, whether the device is a stand-alone consumer product or whether two or more of the devices are used in a system 50. Exposed electrodes 10 can, for instance, be mounted in a grid arrangement 51 on a wall or ceiling of a high traffic area within a private or public space. Unlike the '993 design, a halting of the negative voltage source and a bleeding off of any capacitive charge residing on the exposed electrode 10 is not required due to the presence of user's in the vicinity of the exposed electrode 10.

Additional technical solutions of the invention include quiet fan-less operation and seamless integration of the exposed electrodes 10 into an exposed environment 56. The invention permits an unlimited number of individual panels in a grid arrangement 51 on a wall or ceiling for a distributed and sustained production of NAI.

The aesthetic properties of natural fibres further enhance the ability of the exposed electrodes 10 to be integrated into an exposed environment 56. The consumer can select among panels of various colours and sizes to add to the decor and general ambience of a space. And, unlike house plants, mat surfaces 11 of natural fibres do not cause static shock to the touch and do not require regular watering. The preferred material for the invention, coconut coir, is a low cost renewable agricultural by-product with high NAI emission performance (see FIGS. 7 and 9) whether wet or dry, and whether treated or untreated.

Inclusion of the sensors 52 mounted in the exposed environment 56 and the optional IoT module 22D in each electronics module 22 can additionally provide remote management of the system 50. Sensors 52 can include temperature sensors, humidity sensors, and negative ion concentration sensors. In this manner, feedback from sensors 52 in the exposed environment 56 can be used to optimize the electrical parameters of the devices via an offsite server 55.

The invention's mat surface 11 also enables an NAI design with low ozone emissions, especially for the preferred voltage range of −18 kV to −22 kV. The mat surface 11 has a large number of intertwined individual fibres. Each fibre has rough edges along its length and a sharp distal end creating a large number of locations which act as localized electrodes. With the multiple localized electrodes over the mat surface 11, the maximum preset negative voltage can be reduced while maintaining a high level of NAI emission.

Hygroscopicity of the natural fibres enables sufficient conductivity of natural fibres for suitable NAI generation, as the water content of natural fibres is the primary conductive material of the fibre. Without this water within the fibre, natural fibres would be unsuitable for NAI generation because the resistance of the fibres would be excessively high. Ozone production is likely also reduced from the use of natural fibres as their inherent hygroscopic properties increases the amount of water available at the emitting electrode. Water reacts with ozone to produce short live OH⁻ radicals, and in this process reduces the ozone concentration.

While various aspects and embodiments have been disclosed herein, it will be apparent that various other modifications and adaptations of the invention will be apparent to the person skilled in the art after reading the foregoing disclosure without departing from the spirit and scope of the invention and it is intended that all such modifications and adaptations come within the scope of the appended claims. The various aspects and embodiments disclosed herein are for purposes of illustration and are not intended to be limiting, with the true scope and spirit of the invention being indicated by the appended claims.

The invention claimed is:

1. An exposed electrode negative air ion device, the device comprising:
   (a) an electronics module including an input port, a negative voltage generator, and an output port,
      (i) wherein the input port is configured to electrically receive a power supply and electrically route the power supply to the negative voltage generator;
      (ii) wherein the negative voltage generator is configured to:
         (1) generate a negative voltage source from the power supply; and
         (2) output the negative voltage source to the output port within a set of electrical parameters; and
      (iii) wherein the set of electrical parameters includes:
         (1) a maximum preset negative voltage of $V_{MAX}$; and
         (2) a maximum operating current, the maximum operating current set below or equal to a direct current detection threshold; and
   (b) an exposed electrode, the exposed electrode including a mat surface of intertwined individual fibres,
      (i) wherein the mat surface of the exposed electrode is directly or indirectly electrically connected to the output port of the electronics module at one or more electrical connection points 13; and
      (ii) wherein the mat surface has a minimum mean resistance of $R_{MIN}$, as measured during a discharge event between the output port of the electronics module and a measurement probe, the measurement probe tipped with a polished stainless steel sphere having a diameter of twenty millimetres, where:

$$R_{MIN} = \frac{V_{MAX}}{I_{TH}}; \quad \text{(Equation 1)}$$

and $I_{TH}$ is a capacitive current discharge detection threshold.

2. The device of claim 1, wherein the mat surface is flat in shape and has a maximum surface area of $A_{MAX}$, where:

$$A_{MAX} = \pi \times \left(\frac{Q_{TH}}{V_{MAX} \times 8\epsilon_0}\right)^2; \quad \text{(Equation 3d)}$$

$Q_{TH}$ is a charge discharge detection threshold; and $\epsilon_0$ is permittivity of free space.

3. The device of claim 1, wherein the mat surface is spherical in shape and has a maximum radius of $r_{MAX}$, where:

$$r_{MAX} = Q_{TH}/V_{MAX} \times 4\epsilon_0 \quad \text{(Equation 4b)}$$

$Q_{TH}$ is a charge discharge detection threshold; and $\epsilon_0$ is permittivity of free space.

4. The device of claim 2, wherein the charge discharge detection threshold is 0.4 μC.

5. The device of claim 1, wherein the direct current detection threshold is 2.0 mA.

6. The device of claim 1, wherein the capacitive current discharge detection threshold is 2.0 mA.

7. The device of claim 1, wherein the minimum mean resistance of $R_{MIN}$ is in the range of 10 MΩ to 40 MΩ.

8. The device of claim 1, wherein the intertwined individual fibres are comprised of at least one of coconut coir fibre, hyacinth fibre, jute fibre, abaca fibre, banana fibre, pineapple fibre, and nettle fibre.

9. The device of claim 1, wherein the intertwined individual fibres are comprised of flame retardant coconut coir fibres with:
   (a) a mean diameter in the range of 0.1 mm to 0.5 mm; and
   (b) a mean length in the range of 0.15 m to 0.28 m.

10. The device of claim 1, wherein the intertwined individual fibres are hygroscopic.

11. The device of claim 1, wherein the mat surface of the exposed electrode is at least one of:
   (a) a length of intertwined individual fibres wrapped around a spherical base or a cylindrical base;
   (b) a suspended rope; and
   (c) a rectangular mat.

12. The device of claim 1, wherein the maximum preset negative voltage of $V_{MAX}$ ranges from −18 kV to −22 kV.

13. The device of claim 1, wherein the electronics module is incorporated into the exposed electrode.

14. The device of claim 1,
(a) wherein the exposed electrode includes a conductive base;
(b) wherein the mat surface of intertwined individual fibres is mounted on the conductive base; and
(c) wherein the conductive base is electrically connected to the output port of the electronics module at one or more electrical connection points 13.

15. The device of claim 13,
(a) wherein the exposed electrode includes an insulative perimeter and an insulative surface; and
(b) wherein the conductive base is located between the mat surface and the insulative surface.

16. The device of claim 13, wherein the conductive base comprises a carbon infused elastomer.

17. A negative air ion panel system, comprising two or more of the device of claim 1 mounted in an exposed environment.

18. The system of claim 17, wherein each of the mat surfaces of the devices in the system are configured in at least one of:
(a) a grid arrangement on a wall, a ceiling, or a floor of the exposed environment;
(b) a grouping of spheres or cylinders in the exposed environment; and
(c) a set of individual panel mountings in the exposed environment.

19. The system of claim 17, wherein the power supply of each device is generated by a local solar panel.

20. The system of claim 17, the system further comprising a gateway, a network, and an offsite server, wherein each electronics module of the devices in the system further includes an IoT module in data communication with the offsite server through the gateway and the network.

21. The system of claim 20,
(a) wherein the offsite server further comprises a parameter settings module, the parameter settings module configured to store a latest set of electrical parameters for each device in the system;
(b) wherein the IoT module of each device is configured for wired or wireless data communication to and from the parameter settings module of the offsite server via the gateway and the network;
(c) wherein the parameter settings module is configured to send each device the latest set of electrical parameters for the device; and
(d) wherein each device is configured to receive the latest set of electrical parameters for the device, via the IoT module of the device, from the parameter settings module.

22. The system of claim 20,
(a) wherein the offsite server further comprises a sensor records module;
(b) wherein the system further comprises a plurality of sensors mounted in the exposed environment that are each in data communication with the sensor records module of the offsite server via the gateway and the network; and
(c) wherein the sensors include at least one of:
(i) a temperature sensor;
(ii) a humidity sensor;
(iii) a motion sensor; and
(iv) a negative ion concentration sensor.

23. The system of claim 20,
(a) wherein the offsite server further comprises an analytics module; and
(b) wherein the analytics module is configured to create a system report detailing at least one of:
(i) a history of selected sensor data stored in the sensor records module; and
(ii) a summary of the latest set of electrical parameters for each device in the system.

24. The device of claim 3, wherein the charge discharge detection threshold is 0.4 µC.

* * * * *